United States Patent [19]

Dewey

[11] Patent Number: 4,628,416
[45] Date of Patent: Dec. 9, 1986

[54] VARIABLE SPOT SIZE ILLUMINATOR WITH CONSTANT CONVERGENCE ANGLE

[75] Inventor: David A. Dewey, Huntington Beach, Calif.

[73] Assignee: CooperVision, Inc., Menlo Park, Calif.

[21] Appl. No.: 729,983

[22] Filed: May 3, 1985

[51] Int. Cl.$^4$ .......................... F21V 7/04; A61B 17/36
[52] U.S. Cl. .................................. 362/32; 128/303.1; 128/395
[58] Field of Search .................. 362/32, 259, 268, 277, 362/280, 281, 285, 308, 311; 350/526, 523, 519; 128/395-398, 303.1, 362

[56] References Cited

U.S. PATENT DOCUMENTS

| | | |
|---|---|---|
| 3,068,745 | 12/1962 | Peck . |
| 3,216,807 | 11/1965 | Woodcock . |
| 3,436,142 | 4/1969 | Siegmund et al. . |
| 3,600,568 | 8/1971 | Weyrauch . |
| 3,661,065 | 5/1972 | Yamazaki et al. . |
| 3,669,524 | 6/1972 | Shio . |
| 3,703,176 | 11/1972 | Vassiliadis et al. . |
| 3,720,213 | 3/1973 | Hobart et al. . |
| 3,769,963 | 11/1973 | Goldman et al. ................ 128/395 X |
| 3,930,149 | 12/1975 | French . |
| 4,061,423 | 12/1977 | Pomerantzeff . |
| 4,104,709 | 8/1978 | Kloots . |
| 4,269,485 | 5/1981 | Yamashita et al. . |
| 4,354,734 | 10/1982 | Nakahashi . |
| 4,428,031 | 1/1984 | Mori ....................... 362/32 |
| 4,433,675 | 2/1984 | Konoshima ....................... 362/32 X |
| 4,476,519 | 10/1984 | Hayamizu ............................ 362/32 |
| 4,501,477 | 2/1985 | Sunaga . |
| 4,530,578 | 7/1985 | Kato ................................ 362/32 X |
| 4,538,608 | 9/1985 | L'Esperance, Jr. ............ 128/395 X |

Primary Examiner—Larry Jones
Attorney, Agent, or Firm—Vorys, Sater, Seymour and Pease

[57] ABSTRACT

A variable spot size illuminator for projecting a variable size spot of light into an illumination plane comprises a source of light, fiberoptic image transmission means having an entrance surface and an exit surface, means for projecting a cone of said light onto said entrance surface, objective lens means for focusing light emerging from said exit surface into said illumination plane, and means for varying the distance between said entrance surface and the vertex of said cone of light. The variable spot size illuminator is useful for projecting a spot of variable size with constant beam convergence in a laser photocoagulator.

12 Claims, 6 Drawing Figures

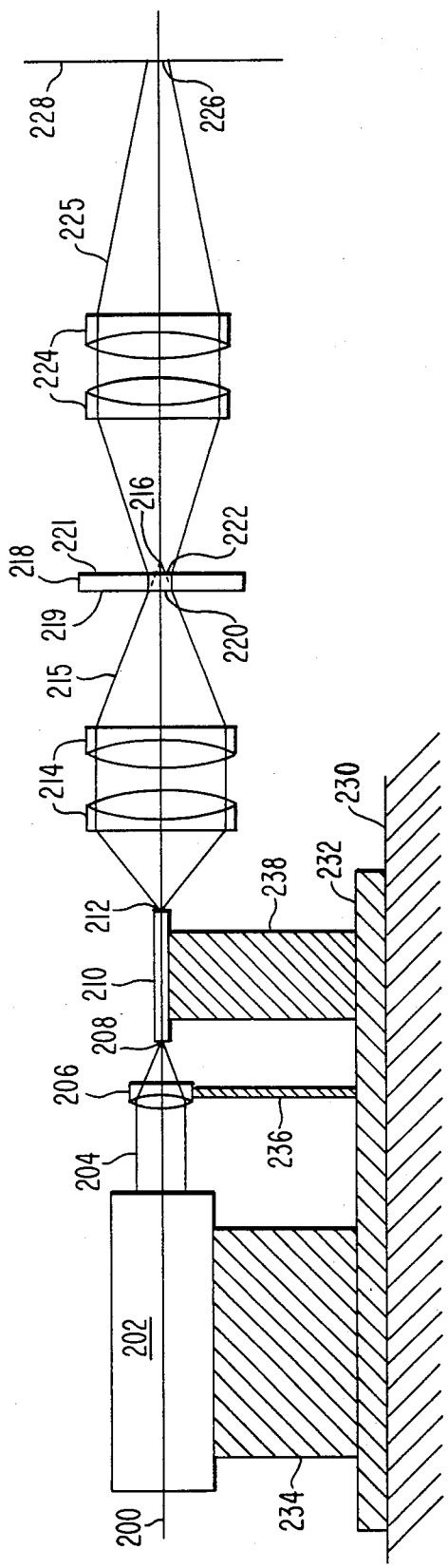
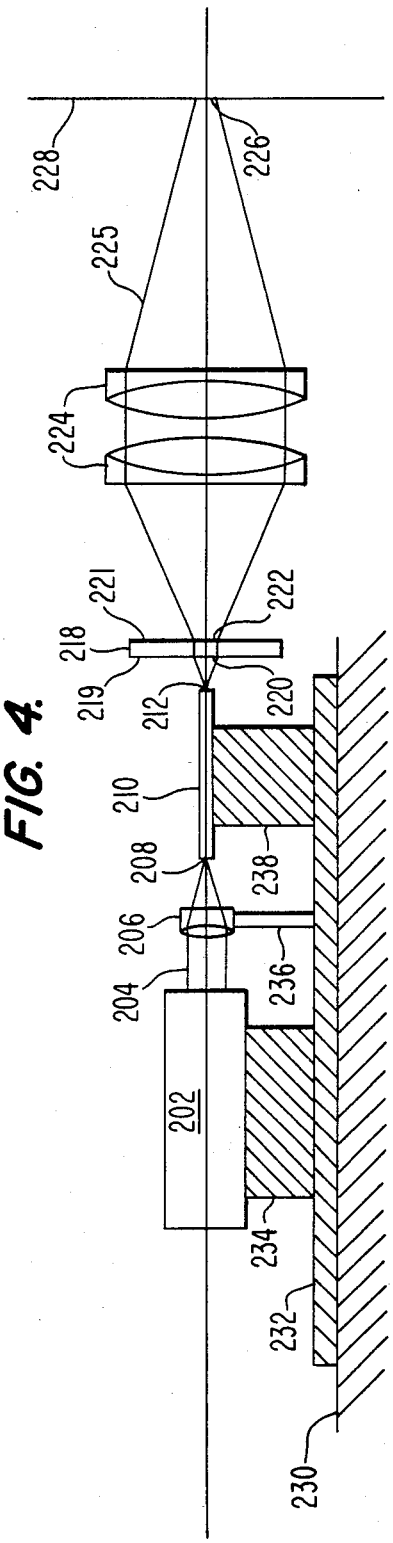

VARIABLE SPOT SIZE ILLUMINATOR WITH CONSTANT CONVERGENCE ANGLE

BACKGROUND OF THE INVENTION

1. Field of the Invention

This invention relates to illuminators capable of illuminating an object plane with a spot of variable size and more particularly to variable spot size illuminators providing a constant convergence angle suitable for use with laser photocoagulators.

2. Description of the Prior Art

Certain surgical procedures on the retina of the eye are performed using a laser photocoagulator combined with a conventional ophthalmological slit lamp. Microscopic lesions are produced in the retina and related tissues by the heating effect of a sharply focused beam of a laser, for example to reattach a detached retina. In these procedures the ophthalmologist observes the fundus of the eye through the slit lamp microscope while directing the laser beam onto the desired portion of the retina by means of a movable mirror. The spot must be small both to keep the area of surgical injury small and to assure that the energy density of the beam is great enough when absorbed by the relatively opaque retina to raise the temperature of the microscopic spot and cause a local coagulation of the tissue. However, to reach the retina the beam must first pass through the anterior portion of the eye, particularly the cornea and crystalline lens, where concentrated absorption of energy is not desired. These structures are relatively transparent, in contrast to the relatively opaque cornea, and therefore do not absorb much energy from the beam. However, for greatest safety it is desirable to have the cross section of the beam in that region as large as possible to keep the energy density low. Under these conditions, any absorbed energy is diffuse and does not cause local heating with injury to the delicate anterior structures of the eye. In order to attain the goal of a high energy density at the retina and a low energy density at the anterior portion of the eye, a convergent beam is formed by an objective lens. The convergent beam has a large cross section when passing through the anterior portions of the eye, but is focused to a high-intensity spot at the retina. The convergent beam therefore minimizes the possibility of injury to the cornea, crystalline lens, and the like.

It is also desirable in laser photocoagulation surgery to vary the focused spot size of the laser beam to produce a larger or smaller area of coagulation as required by a particular surgical procedure. In currently available laser photocoagulators the focus of the objective lens must be adjusted as the spot size is changed. However, in so adjusting the focus of the lens, the convergence angle of the laser beam is necessarily changed. This means that for some settings of the instrument the beam passing through the anterior portions of the eye has a smaller diameter than necessary and a correspondingly greater energy density, which increases the possibility of damage to the anterior portions of the eye. Accordingly, it is desirable to keep the convergence angle of the laser beam at the largest possible value consistent with passing through the anterior portion of the eye while still permitting the spot size to be adjusted.

A further disadvantage of the variable focus mechanism used to adjust spot size in the currently available laser photocoagulators is its relatively complex system of lenses within the instrument.

Variable spot size illuminators are known wherein an illuminated variable aperture is imaged on a plane to be illuminated. Such an instrument adapted to a surgeon's headlamp is disclosed by Kloots, U.S. Pat. No. 4,104,709, who discloses an instrument wherein light is supplied to the headlamp via a fiberoptic cable. The light emerging from the end of the cable is condensed by a condenser lens system and focused onto the objective lens. Immediately after the condensing lens system is located a variable aperture diaphragm of the adjustable iris type which is imaged by the objective lens into the plane to be illuminated. Evidently, while this system is suitable for its intended purpose, the use of a variable aperture diaphragm in this configuration necessarily diminishes the intensity of the illumination when the aperture is reduced. This is undesirable in a laser photocoagulator wherein maximum intensity may be required even with a small spot size.

Another illumination device using a fiberoptic light transmission means is disclosed by Weyrauch, U.S. Pat. No. 3,600,568. In this device, light from a source is imaged by a lens and an image of that lens is projected onto the incidence surface of a fiberoptic light conductor. Light emerging from the fiberoptic light conductor is imaged into the plane to be illuminated. However, Weyrauch does not disclose any means for providing an illuminated spot of variable size in the image plane.

Therefore a need has continued to exist for a variable spot size illuminator suitable for use with a laser photocoagulator which provides convenient variation of the spot size, and constant convergence angle without limitating beam power.

SUMMARY OF THE INVENTION

The objects of the invention have been attained by a variable spot size illuminator comprising
  a source of light,
  fiberoptic image transmission means having an incidence surface and an emergence surface,
  means for projecting a cone of said light onto said incidence surface,
  lens means for focusing light emerging from said emergence surface onto an illumination plane, and
  means for varying the distance between said incidence surface and the vertex of said cone of light.

Accordingly it is an object of this invention to provide an illuminator capable of projecting a variable spot size onto an object.

A further object is to provide an illuminator capable of projecting a variable spot size while maintaining a constant convergence of the illuminating beam.

A further object is to provide a laser photocoagulator for use with a slit lamp.

A further object is to provide a laser photocoagulator wherein the size of the focused spot can be varied while the convergence angle of the beam is kept constant.

Further objects of the invention will become apparent from the description of the invention which follows.

BRIEF DESCRIPTION OF THE DRAWINGS

FIG. 3 illustrates an embodiment similar to FIG. 2 except that the fiberoptic image transmitting plate receives a converging cone of light.

FIG. 4 illustrates an embodiment of the invention wherein the fiberoptic image transmitting plate directly receives a cone of light emerging from a single optical fiber.

DETAILED DESCRIPTION OF THE INVENTION AND PREFERRED EMBODIMENTS

In the variable spot size illuminator of the invention an objective lens projects an image of a variable size light-emitting spot into a fixed image plane. The distance between the spot which is the source of the illumination and the objective lens is fixed, and, accordingly, the distance between the objective lens and the image plane of the projected spot is therefore also constant. In a practical application such as a laser photocoagulator for use with a slit lamp, the spot is focused on the retina of the patient's eye by adjusting the distance between the patient's eye and the objective lens, by moving either the patient's head or the illuminator.

Since in a laser photocoagulator the illuminated spot on the retina is very small, typically from 25 micrometers to 2 millimeters in diameter, while the objective lens has an aperture of a few centimeters, the convergence angle of the beam from the objective lens to the focused spot will not vary appreciably when the spot size is changed, provided that the diameter of the beam at the objective lens and the distance between the lens and the focused spot are both kept constant.

In the illuminator of this invention both these conditions are met by using a light-emitting spot, at a fixed distance from the objective lens, as a source of light for the focused spot. Since the distance from the light-emitting spot to the objective lens is fixed, the distance of the focused spot from the objective lens will also be constant and the angle of convergence of the light rays to the image spot will not vary significantly as the spot size is changed. The device of this invention provides a means whereby the size of the light-emitting spot is changed while keeping the total emitted energy in the spot relatively constant. The beam is merely expanded or contracted to provide a different emitting spot size.

Figure 1:
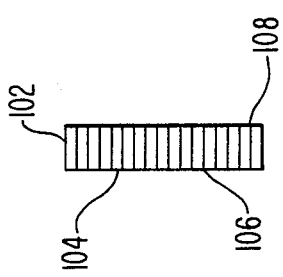
FIG. 1 illustrates an elevational section of a fiberoptic image transmitting plate used in the illuminator of this invention.

The general method by which the variation in emitting spot size is accomplished makes use of a fiberoptic image conducting plate or screen 102 of the type shown in in elevational section in FIG. 1. Such elements are known and are formed of a great many optical fibers 104 packed side by side, each fiber surrounded by a cladding of lower refractive index. In plates of this type the plate is frequently heated after assembly to fuse, at least partially, the cladding of adjacent fibers to form a monolithic unit. Each fiber originates at an entrance face 106 and terminates at an exit face 108. The fibers are laid parallel to one another whereby they retain their same relative positions at the entrance and exit faces. Accordingly, an image projected onto the entrance face of the fiberoptic image transmitting plate appears unchanged and undistorted on the exit face. Because of this property of transmitting images, fiberoptic plates of this type are sometimes called "coherent". In some devices of this type, the fibers may taper, so that the image on the exit face is of a different size than that on the incidence face, but the shape of the image will not change. The fiberoptic image transmitting element used in the device of this invention may be of any suitable thickness. However, it is preferred that the fiberoptic image transmitting element be an assembly of short optical fibers packed parallel to one another, each fiber end terminating in a planar surface which serves as the entrance face or the exit face. Such fiberoptic imaging plates are known and are commercially available. Although planar entrance and exit surfaces are generally preferred in the fiberoptic image transmitting element, either the entrance face or the exit face may be convex or concave, if desired, to better match the convergence or divergence of the light rays and present to each incident ray a surface generally perpendicular thereto.

The diameter of the optical fibers making up the fiberoptic image transmitting plate may vary from a about 6 micrometers to about 100 micrometers. A preferred range is about 14 micrometers to about 50 micrometers, while a still more preferred diameter is about 14 micrometers. The fibers are clad with a material of lower refractive index in order to insure their light conducting properties even when they are in contact with adjacent parallel optical fibers. In order to maximize light transmission it is preferred that the packing fraction of the fiberoptic image transmitting plate, i. e., the fraction of the entrance and exit surfaces occupied by the light transmitting fibers be as high as possible. It is possible to make fiberoptic plates of this type having packing fractions as high as 0.90–0.95, and such plates are preferred. In order to assure maximum light transmission, the glass frit used to fill in the interstices between the clad fibers and bond the fibers together should not contain any light absorbing material as is sometimes introduced into such image transmitting plates.

Figure 2:
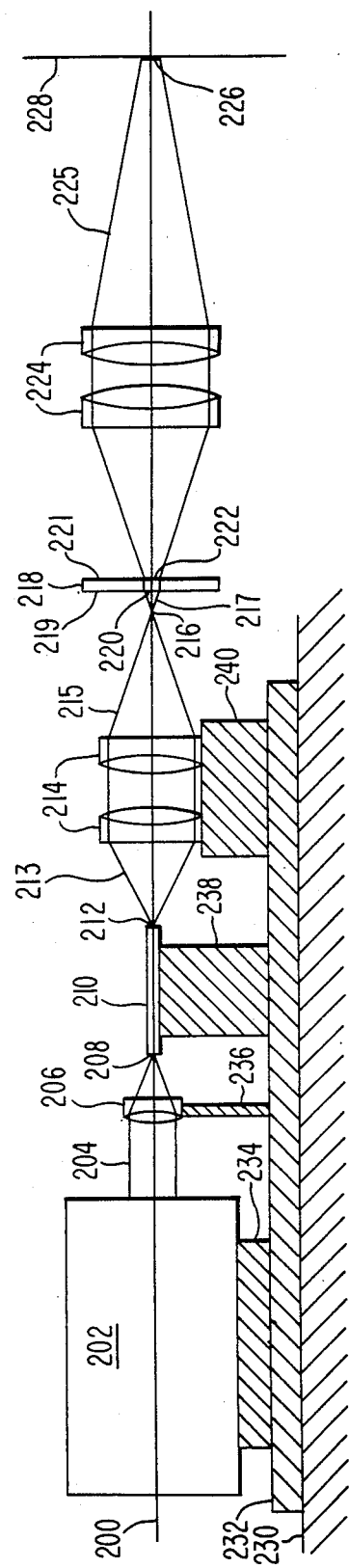
FIG. 2 illustrates an embodiment of the invention wherein the incidence surface of the fiberoptic image transmitting plate receives a diverging cone of light generated by a lens system which focuses the light emerging from a single optical fiber.

In the embodiment of the invention illustrated in FIG. 2 a laser 202 serves as a source of light to provide a beam of collimated light 204. This beam is focused by lens 206 onto the entrance end 208 of a single optical fiber 210. The single fiber may have a diameter of about 10 to about 2000 micrometers, preferably about 50 micrometers. While the optical fiber 210 is described herein as being a single optical fiber since it is entirely illuminated by the light focused on its entrance end 208, it will be understood by those skilled in the art that it may comprise a small bundle of generally parallel optical fibers, which, however, need not be coherent in the same sense as those forming the fiberoptic image transmitting element 218. In this case, the total diameter of the bundle should be as described above. Light emerging from the exit end 212 of the optical fiber 210 will form a diverging cone of light 213. This diverging cone is focused by condensing lenses 214 to form a converging cone of light 215 which is focused at a vertex 216 and diverges beyond the vertex 216 in a diverging cone of light 217. The diverging cone of light 217 is incident on the entrance face 219 of a fiberoptic image transmitting plate 218, forming an illuminated spot 220 on the entrance face 219. The light received by the entrance face 219 is tranmitted by the fiberoptic imaging plate 218 to the exit face 221 of the plate 218, where it forms light-emitting spot 222. Since the fiberoptic plate 218 is capable of transmitting an image from the entrance face 219 to the exit face 221, the emitting spot 222 will in general be of the same size as the incident spot 220. The light emitted by the spot 220 is collected by the objective lens means, shown in FIG. 2 as a doublet comprised of lenses 224. The objective lens means focuses the light emitted by the spot 220 as an image 226 of the spot 220 in an image plane 228. The ratio of the size of the image spot 226 to the source spot 220 is determined by the spacing of the objective lens means 224 from the exit surface 221 of the fiberoptic image transmitting plate 218. Since this spacing is fixed in a given illuminator the ratio of spot sizes is constant. For the same reason the angle of convergence of the cone of light 225 leaving the objective lens means is also constant in a given instrument.

In order to vary the size of imaged illumination spot 226 in image plane 228, means are provided to vary the size of source spot 222 by varying in turn the size of the incidence spot 220 on the entrance face 219 of the fiberoptic image tranmitting plate 218. The size of incidence spot 220 is varied by changing the distance between the incidence face 219 and the vertex of the incident cone of light 217. As the distance between the vertex 216 and the entrance face is increased the size of the incident spot 220 will also increase, and vice versa. The size of the source spot 222 on the exit face of the fiberoptic plate 218 and will vary exactly as the incidence spot 220, and the size of the image spot 226 will vary in proportion.

Means for varying the distance between the entrance face of the fiberoptic plate 218 and the vertex 216 of the light cone 217 are also shown schematically in FIG. 2. A base 232, movable on a supporting surface 230, is shown with mounting means 234, 236, 238, and 240 for laser 202, focusing lens 206, optical fiber 210 and condensing lens means 214 respectively. The base 232, with its supported components can be moved parallel to the optical axis 200 of the illuminator to vary the distance between the entrance face 219 of the fiberoptic image transmitting plate 218 and the vertex 216 of the cone of light 217. Variation of this distance produces a corresponding variation of the size of incident spot 220 and consequently of illuminating spot 226, as explained above. In this schematic embodiment the fiberoptic plate 218 and objective lens means 224 are considered as fixed with respect to each other by being supported on conventional supports not shown.

In order to provide the maximum convergence angle for the beam 225 between the objective lens means 224 and the focused spot 226, the beam should fill the aperture of the objective lens means 224. Accordingly, the cone of light emerging from the illuminated spot 222 on the exit face 221 should substantially fill the aperture of the objective lens means 224. The divergence angle of the cone of light emerging from the exit face 221 of the fiberoptic plate 218 will be determined by the properties of the optical fibers in the plate, the focal length of the condenser lens 214 and the divergence angle of the cone of light 213 emerging from the exit end of optical fiber 210. In turn, the divergence angle of the cone of light 213 is determined by the properties of the optical fiber 210 and the focal length of the focusing lens 206. The factors controlling the angle of divergence of a cone of light emerging from an optical fiber are basically three: (1) entering cone angle, (2) inherent spreading of the fiber core, and (3) limiting numerical aperture (N. A.) of the fiber. The entering cone angle (1) establishes a minimum exit cone angle and is controlled by the laser beam diameter and the focal length of the focusing lens 206 which focuses the laser light onto the input end 208 of the optical fiber 210. However, the other two factors can contribute to a wider diverging cone angle of the emergent beam. The second factor, inherent spreading of the fiber core, depends on the fiber construction, type and quality. Light tends to spread in the fiber core due to variations in the fiber core refractive index, scattering from inclusions and surface defects, micro fractures, and bending of the fiber. All of these effects are cumulative with the length of the fiber and contribute to greater spreading for a greater fiber length. The third factor, the basic limiting angle transmissible by the fiber, results from the difference between the refractive index of the core and the cladding. Light having an angle with respect to the optical axis of the fiber greater than that corresponding to the fiber N. A. escapes from the core and is lost from the fiber. Therefore the fiber N. A. establishes a maximum divergence angle. Consequently, the fiber used to supply light to the condensing lens system 214 or directly to the fiberoptic plate 218 as discussed below in connection with the embodiment of FIG. 4 should preferably have a limiting N. A. matched to the entrance convergence angle and to the numerical apertures of the other optical components of the system. In particular, the limiting N. A. must be greater than or equal to the N. A. corresponding to the input light convergence. Preferably, a fiber is used wherein the inherent spreading (factor (2)) is negligible over the length of the fiber. Making use of these considerations, the choice of the focal lengths (numerical apertures) of the individual lenses and the properties of the optical fibers is easily accomplished by the skilled designer in a given situation.

Another embodiment of the invention is illustrated in FIG. 3, which shows a slightly different means for varying the size of incident spot 220 on the entrance face 219 of the fiberoptic plate 218. In this embodiment the beam from the laser light source 202 is focused onto the entrance end 208 of optical fiber 210, and the light emitted from the exit end 212 of optical fiber 210 is collected by condensing lens means 214 which form a converging cone of light 215 just as in the embodiment of FIG. 2. However, in this embodiment the converging cone is incident on the entrance face 216 of the fiberoptic plate 218 before it reaches the vertex 216. In this embodiment the vertex 216 is merely geometrical, since the rays of the converging cone of light 215 never reach the vertex 216. The vertex 216 may be considered to be a virtual image in this embodiment and its location is indicated by the dotted lines in FIG. 3. However, the size of the incident spot 220 still varies with the distance between the vertex 216 and the entrance face 219 of the fiberoptic plate 218, just as in the embodiment of FIG. 2.

FIG. 3 also illustrates another method of varying the distance between the vertex 216 and the entrance face 219 of the fiberoptic plate 218. In this embodiment the movable base 232 supports only the laser 202, the focusing lens 206 and the single optical fiber 210. The condenser lens means 214, the fiberoptic plate 218 and the objective lens means are fixed with respect to one another and are considered to be supported in fixed relationship by conventional support means not shown. Since the vertex 216 of the cone of light 215 is the image of the light source which is the light emitting end 212 of optical fiber 210, its location with respect to condensing lens means 214 is determined by the laws of optics and the distance between the source of light and the lens means 214. According to these optical laws, as the source 212 approaches the lens means 214 the real image of the source which is the vertex 216 moves further away from the lens means 214. Conversely, as the source 212 is moved further away from condensing lens means 214, the image of the source, vertex 216, moves closer to lens means 214. Since the distance between lens means 214 and the entrance face 219 of the fiberoptic plate 218 is fixed in this embodiment, the position of the vertex 216 with respect to the entrance face 219 is varied, and the size of the incident spot 220 is varied accordingly. This variation in the size of the incidence spot 220 produces a corresponding variation in the size of the imaged spot 226 as explained above for the embodiment of FIG. 2.

FIG. 4 illustrates an embodiment of the invention wherein the diverging cone of light 213 emerging from the exit end of optical fiber 210 is used directly as the cone of light which is incident on the entrance face 219 of fiberoptic plate 218. In this case the vertex of the cone of light 213 is located at the exit end 212 of the optical fiber 210. In this embodiment the laser light source 202, the focusing lens 206 and the optical fiber 210 are moved as a unit to vary the distance between the vertex of the cone of light 213 and the entrance face 219 of the fiberoptic plate 218. Again it is evident that variation in this distance will produce a variation in the size of the incidence spot 220 on the entrance face 219 of the fiberoptic plate 218.

Figure 5:
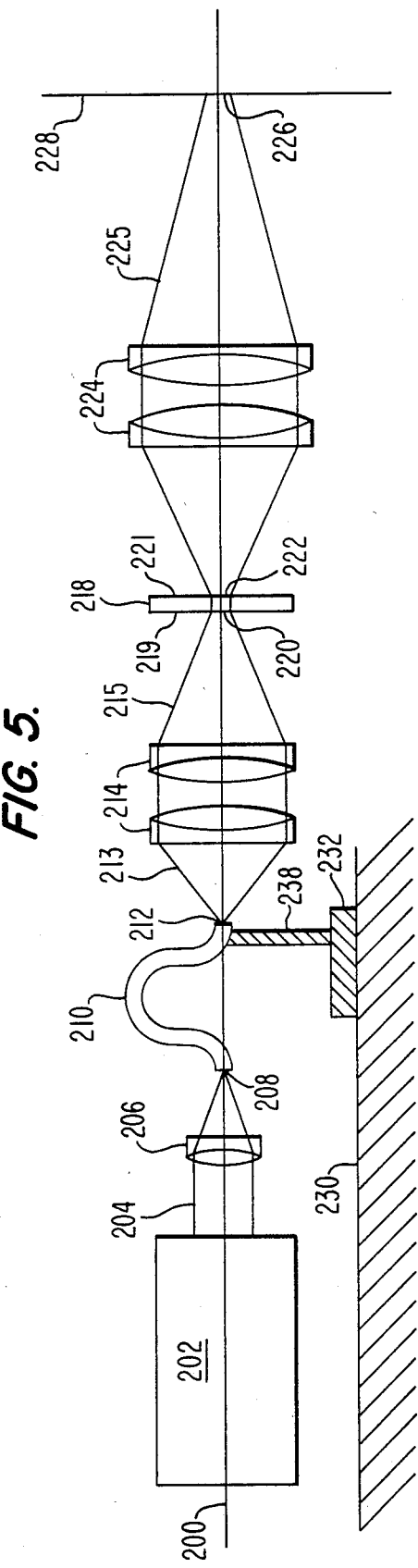
FIG. 5 illustrates an embodiment of the invention wherein the single optical fiber is flexible so that only the emergence end of the fiber is moved.

FIG. 5 illustrates an embodiment of the invention wherein the optical fiber 210 is a flexible optical fiber which, as is well known, conducts light through a curved path with little or no attenuation. Accordingly, when such a flexible optical fiber is used as the optical fiber 210, it is only necessary that the entrance end 208 of the optical fiber 210 receive the focused illumination of the laser light source 202 and that the exit end 212 be located on the optical axis of the illuminator facing in a direction to send the emerging light to the condensing lens means 214 as shown in FIG. 5 as well as in FIGS. 2, 3 and 4.

Figure 6:
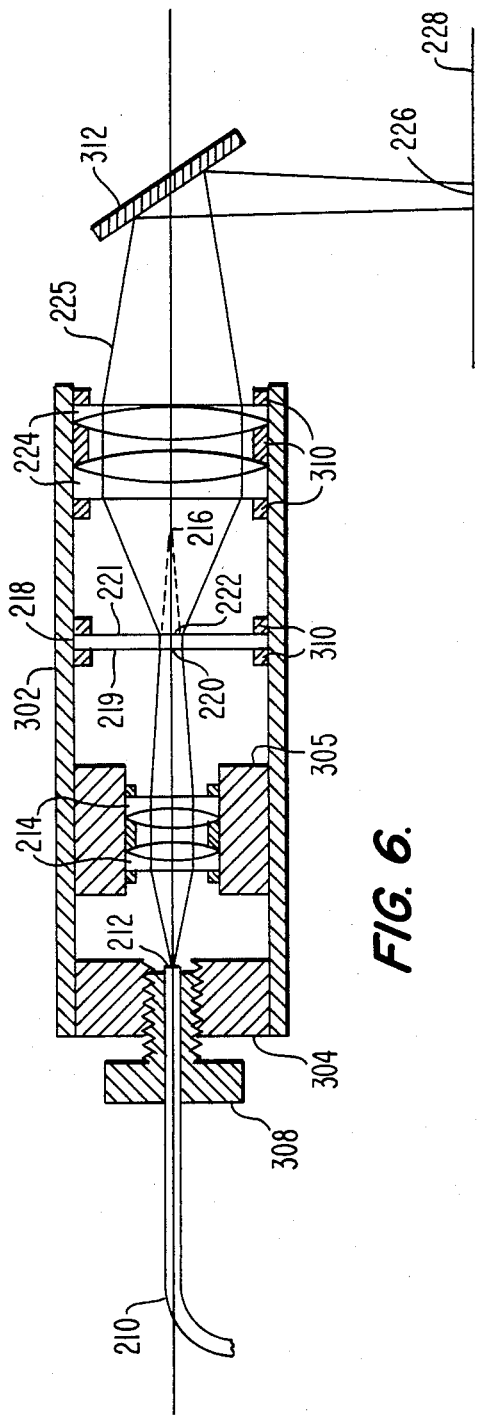
FIG. 6 illustrates an embodiment of the invention adapted to be used with a remote source of light as in a laser photocoagulator for use with a slit lamp.

FIG. 6 illustrates, in elevational cross section, an embodiment of the invention more adapted for use with an optical instrument such as a slit lamp. The optical elements are shown mounted in a tube 302 made of metal or other rigid material. The objective lens means 224, the condensing lens means 214 and the fiberoptic plate 218 are mounted in the tube by conventional means, for example by retaining and spacing rings 310 as shown. The tube 302 can be adapted for mounting of lenses of various diameters as desired by fitting internal lens mounting bushings 305 as required. In this embodiment the optical fiber 210 takes the form of a fiberoptic cable which brings light from a remote source of light, e.g., a remotely located laser with focusing lens, not shown in this figure, to the illuminator. The exit end 212 of the optical fiber 210 is located on the optical axis of the illuminator where it serves as the source of light used by the condensing lens means 214 to form the converging cone of light 215. The exit end 212 of the optical fiber 210 is mounted in an externally threaded fitting 308 which is inserted into internally threaded bushing 304. By turning the threaded fitting 308 in the bushing 304 the distance of the exit end 212 of the optical fiber 210 from the condensing lens means 214 is varied to change the diameter of the illuminated spot 226 as discussed above in connection with the embodiment of FIG. 5. This embodiment also illustrates the use of mirror 312 to turn the focused beam approximately through a right angle for more convenient use as an accessory for an optical instrument such as a slit lamp. By changing the inclination of the mirror using mounting and directing means which are conventional and not shown, the illuminated spot can be directed to various locations in the image plane 228, for example, to various locations on the retina of an eye.

In the drawings the lenses have been shown as being of the achromatic type, which are useful to avoid chromatic aberration when a polychromatic source of light, e.g., white light, is used or shifts in focus when the illuminator is to be used with different monochromatic light sources, e.g., with a plurality of lasers each emitting light of a different wavelength. However, it will be understood by those skilled in the art that when the illuminator is to be used with a light source of a single wavelength, simple lenses may be used with good results.

The embodiments illustrated show the use of an optical fiber in generating the cone of light which is projected onto the entrance face of the fiberoptic image transmission means. However, it will be recognized by the skilled practitioner that any means capable of projecting a converging or diverging cone of light onto the entrance face, e.g., a collimated beam of light and a lens movable along the optical axis, may be used in the apparatus of this invention.

While the invention has been described in terms of it use with light, it is evident that it is not restricted to use with light of visible wavelengths only. By suitable choice of radiation sources and materials for the optical components the illuminator can be used with ultraviolet or infrared radiation as well.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A variable spot size illuminator for projecting a variable size spot of light into an illumination plane comprising
   a source of light,
   fiberoptic image transmission means having an entrance surface and an exit surface,
   means for projecting a cone of said light onto said entrance surface,
   objective lens means for focusing light emerging from said exit surface into an illumination plane, and
   means for varying the distance between said entrance surface and the vertex of said cone of light.

2. The illuminator of claim 1 wherein said source of light is a laser.

3. The illuminator of claim 1 wherein said fiberoptic image transmission means is a fiberoptic imaging plate.

4. The illuminator of claim 1 wherein said means for projecting a cone of light comprises an optical fiber light conductor having an entrance end and an exit end, lens means for focusing light from said source onto said entrance end, and lens means for projecting a cone of light from said exit end of said optical fiber light conductor.

5. The illuminator of claim 4 wherein said lens means for projecting a cone of light comprises a pair of lenses.

6. The illuminator of claim 5 wherein said lenses are plano-convex lenses.

7. The illuminator of claim 5 wherein said lens means for projecting a cone of light from said light-emitting end of said optical fiber light conductor comprises a pair of achromatic lenses.

8. The illuminator of claim 4 wherein said optical fiber light conductor is a flexible optical fiber.

9. The illuminator of claim 8 wherein said means for varying the distance between said vertex of said cone of light and said entrance face comprises means for moving the exit end of said flexible optical fiber light conductor.

10. The illuminator of claim 1 additionally comprising a mirror between said objective lens means and said illumination plane plane for positioning said focused light from said exit surface of said fiberoptic image transmission means.

11. A laser photocoagulator having a variable spot size with substantially constant beam convergence angle for use with a slit lamp comprising laser source of light, flexible optical fiber means having an entrance end which receives light form said laser and an exit end from which said received light emerges, fiberoptic image transmission means having an entrance surface and an exit surface, means for projecting a cone of said light onto said entrance surface, objective lens means for focusing light emerging from said exit surface into an illumination plane, and means for varying the distance between said entrance surface and the vertex of said cone of light.

12. The laser photocoagulator of claim 11 further comprising a movable mirror between said objective lens means and said illumination plane.

* * * * *